(12) United States Patent
Levine et al.

(10) Patent No.: US 11,273,318 B1
(45) Date of Patent: *Mar. 15, 2022

(54) WIRELESS TEETH WHITENING SYSTEM

(71) Applicant: JBL RADICAL INNOVATIONS, LLC, New York, NY (US)

(72) Inventors: Jonathan B. Levine, New York, NY (US); Jordan Goncalves, Brooklyn, NY (US)

(73) Assignee: GLO SCIENCE, INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/174,553

(22) Filed: Feb. 12, 2021

(51) Int. Cl.
*A61N 5/06* (2006.01)
*H05B 45/30* (2020.01)
*A61F 7/00* (2006.01)
*A61H 23/02* (2006.01)
*A61H 21/00* (2006.01)
*H05B 47/19* (2020.01)

(52) U.S. Cl.
CPC .............. *A61N 5/0603* (2013.01); *A61F 7/00* (2013.01); *A61H 21/00* (2013.01); *A61H 23/02* (2013.01); *A61N 5/0613* (2013.01); *H05B 45/30* (2020.01); *H05B 47/19* (2020.01); *A61F 2007/0017* (2013.01); *A61H 2201/10* (2013.01); *A61H 2201/501* (2013.01); *A61H 2201/5092* (2013.01); *A61H 2201/5097* (2013.01); *A61H 2230/655* (2013.01); *A61N 2005/0606* (2013.01); *A61N 2005/0626* (2013.01); *A61N 2005/0652* (2013.01); *A61N 2005/0663* (2013.01)

(58) Field of Classification Search
CPC .................. A61C 19/06; A61C 19/066; A61N 2005/0606; A61N 2005/0652; A61N 5/0603
See application file for complete search history.

(56) References Cited

U.S. PATENT DOCUMENTS

| 9,566,140 | B2 * | 2/2017 | Brown | .................. | A61C 17/20 |
| 9,636,198 | B2 * | 5/2017 | Kodama | .............. | A61C 19/063 |
| 10,918,470 | B1 * | 2/2021 | Levine | ................. | A61C 19/066 |
| 2019/0388208 | A1 * | 12/2019 | Whitney | ................ | A61C 19/02 |

* cited by examiner

*Primary Examiner* — John P Lacyk
(74) *Attorney, Agent, or Firm* — H. Jay Spiegel

(57) ABSTRACT

A wireless teeth whitening system includes a mouthpiece that is devoid of any electrical circuitry so that it may easily be cleaned and sterilized. A control module may be coupled to the mouthpiece. This module has an electrical circuit board with LEDs and heating elements mounted on it. When the control module is coupled to the mouthpiece, the system may be used to whiten teeth. The control module includes a battery that may be inductively charged, and may be wirelessly controlled via Bluetooth from a mobile application.

22 Claims, 7 Drawing Sheets

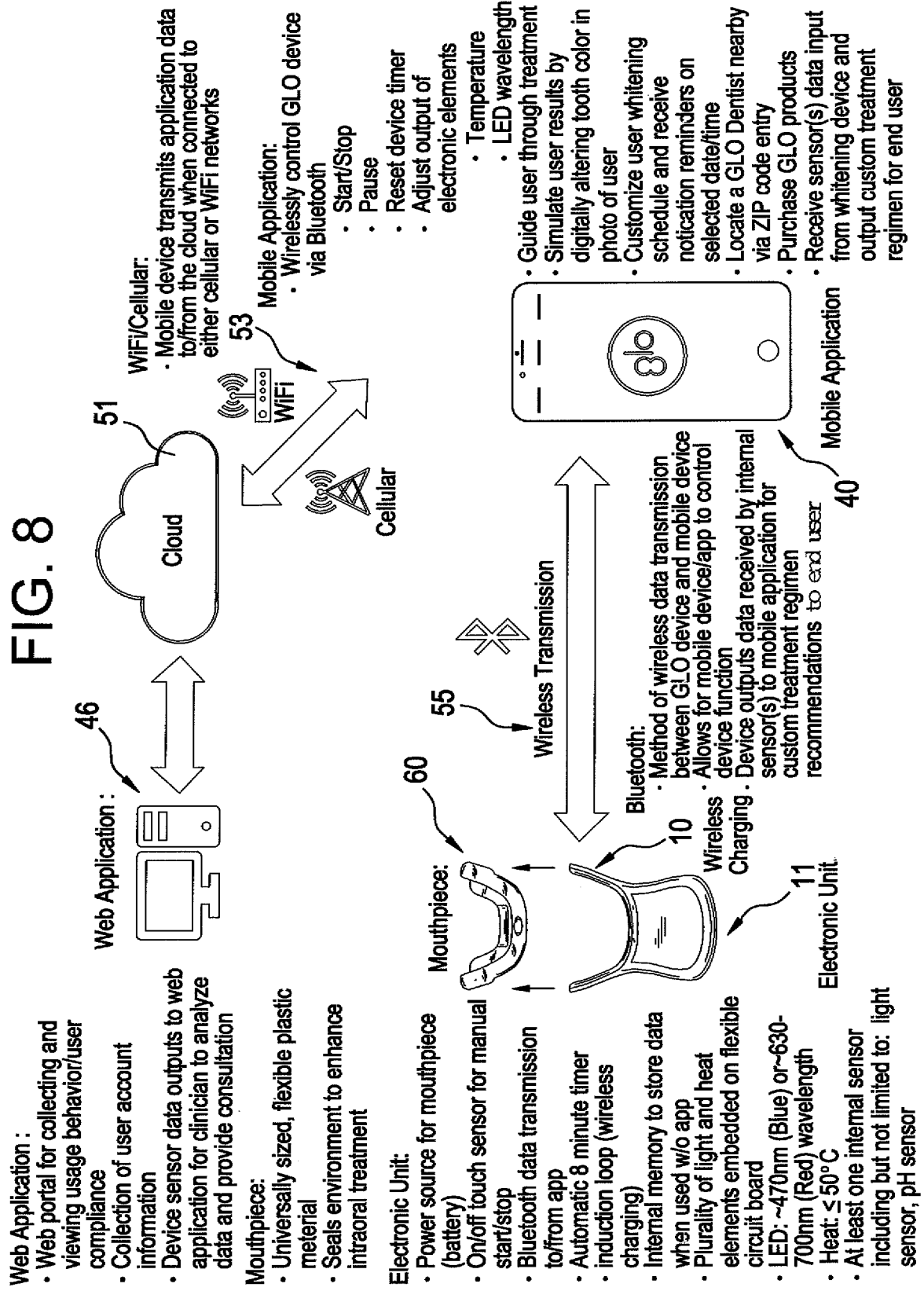

WIRELESS TEETH WHITENING SYSTEM

This application is a Divisional of application Ser. No. 16/593,104, filed Oct. 4, 2019, and issued on Feb. 16, 2021 as U.S. Pat. No. 10,918,470. The present invention relates to a wireless teeth whitening system. Co-inventor Jonathan B. Levine, DMD is a pioneer in the field of whitening teeth using mouthpieces including emission of blue light and heat. As sole inventor in U.S. Pat. Nos. 8,029,278; 8,371,853; and 8,591,227, and as a co-inventor in U.S. Pat. Nos. 9,572,645; 9,827,174; and 10,123,860, Dr. Levine pioneered creating a mouthpiece with a flexible circuit board embedded therein and including a bite tab with a row of LEDs aligned with the bite tab, and rows of heating resistors above and below the row of LEDs. The LEDs are/were designed to emit blue light at a wavelength of approximately 470 nm. After this innovation took the marketplace by storm, competitors began introducing competing designs which, to avoid infringing the above-mentioned patents, reversed the orientation of the LEDs and heating elements, providing a row of heating elements aligned with the bite tab and rows of LEDs above and below. Such devices have been less effective in whitening teeth than is the case with Dr. Levine's innovations mainly because providing only a single row of heating elements aligned with the bite tab limits the ability of a mouthpiece to elevate its temperature to approximately 50° C., a temperature necessary to effectively whiten teeth.

BACKGROUND OF THE INVENTION

One aspect Dr. Levine's mouthpieces and those of the competition have in common is that they all require an electrical conductor connected to a source of power via a transformer in order to operate. Moreover, none of these devices has any ability to provide haptic or tactile feedback, collect data via embedded optical and/or electrical sensors, emit multiple wavelength settings to effect particular treatments, nor to allow remote control of operation and remote monitoring. Additionally, those devices that use a controller connected by an electrical conductor that includes an internal battery require the internal battery to be recharged separately from the mouthpiece.

As such, a need has developed for a more convenient tooth whitening mouthpiece that allows wireless use, remote monitoring and control, and includes additional features including vibration, inductive charging, a mouthpiece that may be removed from the electrical circuitry for cleaning and sterilization, and other aspects such as embedded sensor(s) for treatment data collection and LEDs emitting various wavelengths designed for particular treatment efficacies. It is with these needs in mind that the present invention was developed.

SUMMARY OF THE INVENTION

The present invention relates to a wireless teeth whitening system. The present invention includes the following inter-related objects, aspects and features:

(1) In a first aspect, a mouthpiece is provided including a bite tab allowing engagement by the upper and lower teeth to hold the mouthpiece in place. The mouthpiece is devoid of any electrical circuitry and may easily be cleaned and sterilized without damaging any electrical components.

(2) The mouthpiece has a rear side including a bite tab extending rearwardly. In the preferred embodiment, the bite tab is continuous but, if desired, it may be segmented.

(3) The forward side of the mouthpiece includes an elongated arcuate slot or recess which is sized to receive the rear portion of a control module. The control module includes on its rearmost face a circuit board arcuately disposed thereon which includes a row of LEDs centrally located and rows of heat resistors or heating elements above and below the row of LEDs. Thus, when the control module is assembled to the mouthpiece, the rear face of the circuit board engages a forward surface of the slot or recess in the mouthpiece so that the LEDs are aligned with the bite tab and the rows of heat resistors are above and below the bite tab.

(4) The control module includes an inductive charging coil connected to an internal battery that may be wirelessly charged inductively by placing the control module on or adjacent a charging pad. The battery is electrically connected to the LEDs and heating resistors.

(5) The control module includes a transmitter and receiver allowing communication, for example, by what is known as "Bluetooth" to allow both control of the control module remotely as well as transmission from the control module of data as desired.

(6) The control module also includes a vibrating motor allowing the control module to vibrate and thereby impart vibration to the mouthpiece for user feedback including haptic (tactile) feedback and various therapeutic purposes. A timer is also provided which may be set remotely to facilitate setting the time period within which the mouthpiece will transmit heat and light via the control module to the oral cavity and teeth of the wearer. The timer may also time the operation of the vibrating motor.

(7) Additionally, the control module may either directly or via Bluetooth be controlled to allow starting and stopping of heat and light, pausing during a cycle of whitening, resetting a timer and changing the duration on the timer, controlling activation and deactivation of vibration feature, and controlling outputting of information from the control module concerning history of operation thereof.

As such, it is a first object of the present invention to provide a wireless teeth whitening system.

It is a further object of the present invention to provide such a system in which a mouthpiece is devoid of any electrical circuitry to facilitate cleaning and sterilization.

It is a yet further object of the present invention to provide such a system in which a control module can be removed from the mouthpiece for cleaning and sterilization of the mouthpiece and can then be attached back onto the mouthpiece.

It is a still further object of the present invention to provide such a system in which the control module includes an arcuate electrical circuit on which LEDs and heating elements are suitably provided.

It is a still further object of the present invention to provide such a system in which the control modules, LEDs and heating elements are so situated that they engage a forward surface of the mouthpiece when the mouthpiece and control module are assembled together.

It is a still further object of the present invention to provide wireless control of the system from a remote location.

It is a yet further object of the present invention to provide such a system in which one may recharge a battery included in the control module through inductive charging.

It is a yet further object of the present invention to provide such a system in which monitoring and memorializing a schedule of teeth whitening may be carried out.

These and other objects, aspects and features of the present invention will be better understood from the following detailed description of the preferred embodiment when read in conjunction with the appended drawing figures.

BRIEF DESCRIPTION OF THE DRAWINGS

FIG. 5a shows a front view of the mouthpiece and FIG. 5b shows a cross-sectional view along the line 5b-5b of FIG. 5a.

FIG. 8 shows a schematic representation of the wireless teeth whitening system including actuator and remote aspects.

SPECIFIC DESCRIPTION OF THE PREFERRED EMBODIMENT

Figure 1:
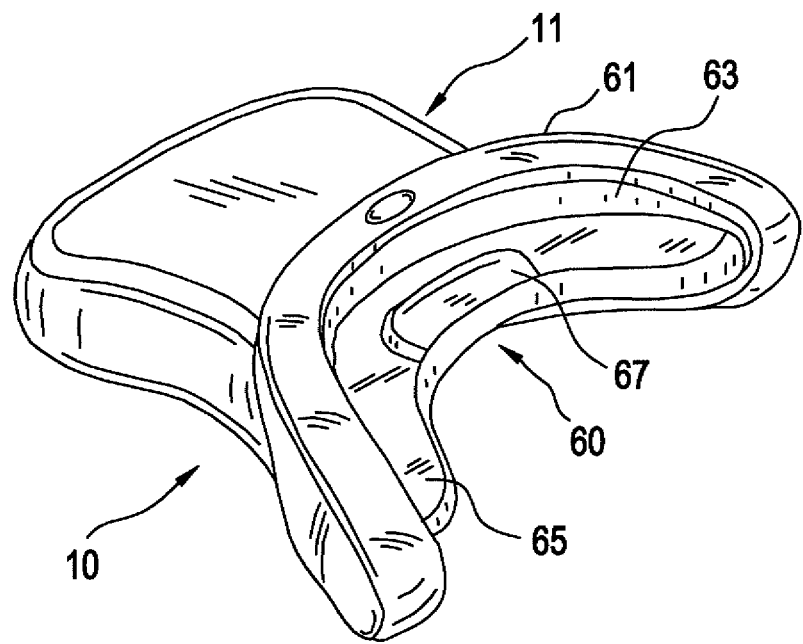
FIG. 1 shows a perspective view of the control module and mouthpiece as assembled together.

Reference is first made to FIG. 1 which shows the wireless teeth whitening system control module and mouthpiece collectively as reference numeral 10 with the control module being referred to by reference numeral 11, and the mouthpiece being generally represented by the reference numeral 60. The mouthpiece includes a forward facing surface 61, a rearward facing surface 63, and a bite tab 65 with an upstanding protuberance 67. As clearly seen in FIGS. 1-3, the forward facing surface 61 includes rearwardly extending side surface portions in the rearwardly extending sides of the mouthpiece 60.

Figure 2:
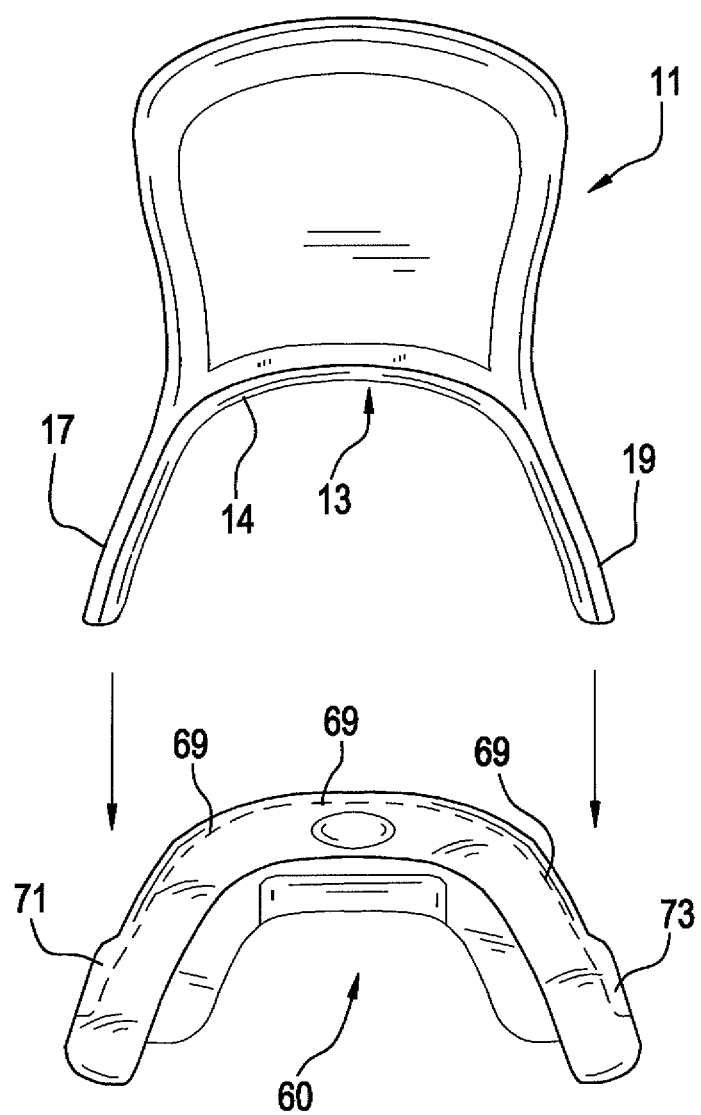
FIG. 2 shows a top exploded view of the mouthpiece and control module.
Figure 3:
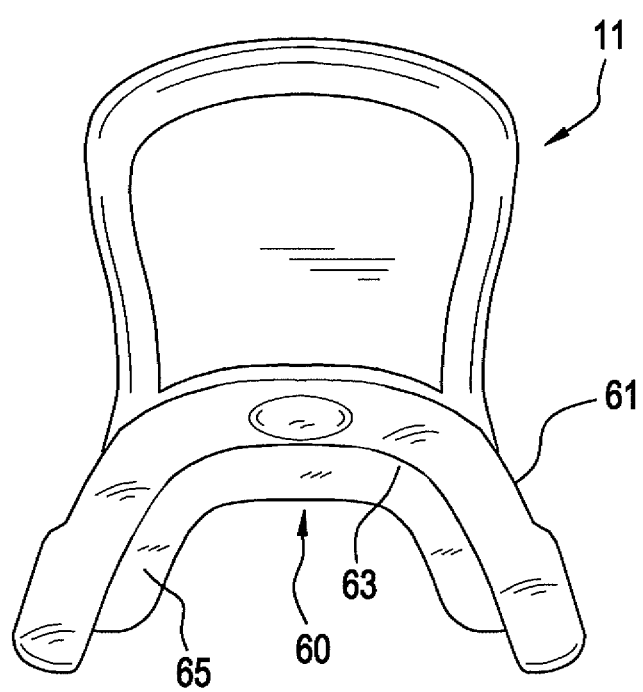
FIG. 3 shows a bottom view of the mouthpiece and control module as assembled together.
Figure 5A:
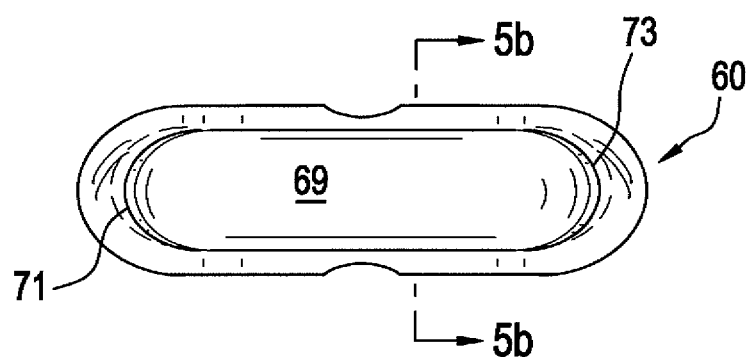
Figure 5B:
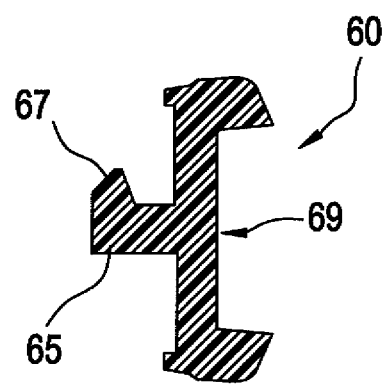

With reference to FIGS. 2, 5a and 5b, the mouthpiece 60 includes a forward slot or recessed area 69 which is arcuate in nature and includes recessed areas or pockets 71 and 73 located within the rearwardly extending sides of the mouthpiece 60 (FIGS. 2 and 5a) for a purpose to be explained below.

Figure 4:
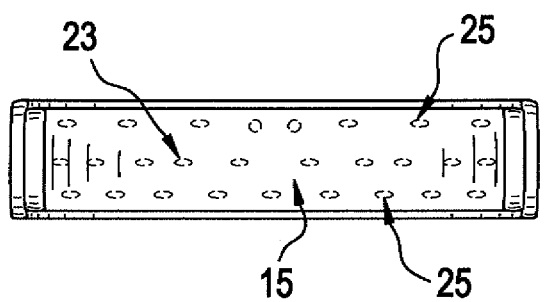
FIG. 4 shows a rear view of the control module with the electrical circuit board visible.

With reference to FIG. 2, the control module 11 includes an arcuate rearward surface 13 including a central portion 14, and the electrical circuit board 15 (FIG. 4) is exposed at the surface 13. The circuit board 15 is arcuate corresponding to the arcuate nature of the surface 13. The control module 11 (FIG. 2) includes rearwardly extending fingers or wings 17 and 19 which enter the recesses or pockets 73 and 71, respectively, when the control module 11 is coupled to the mouthpiece 60. When so coupled, the surface 13 matches the arcuate surface 69 (FIG. 5) of the mouthpiece so that they are substantially flush against one another. In this way, light from the LEDs 23 shines through the transparent or translucent mouthpiece 60 and into the oral cavity. Similarly, heat emanating from the heating elements or heat resistors 25 (FIG. 4) flows through the mouthpiece 60 by convection, exposing the oral cavity to elevated heat.

Figure 6:
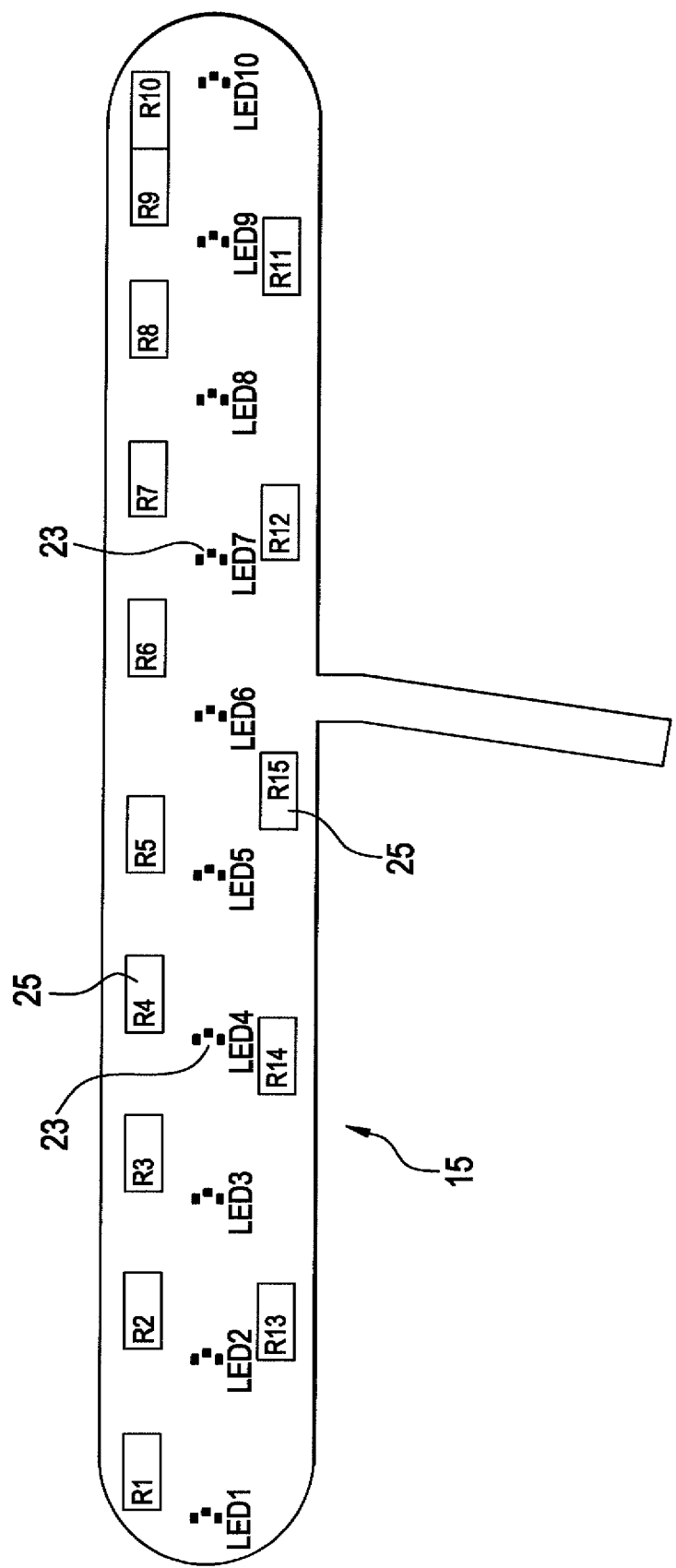
FIG. 6 shows a rear view of the circuit board showing LEDs and heating resistors.

The arcuate electrical circuit 15 is best seen with reference to FIG. 6 and in FIG. 6, ten LEDs are shown as well as fifteen heating resistors. These numbers are exemplary. Locating the LEDs aligned with the bite tab 65 most effectively causes blue light at a wavelength of 470 nm or red light at a wavelength within the range of 630-700 nm to illuminate the interior of the oral cavity. Locating the heat resistors or heating elements 25 above and below the bite tab 65 is advantageous because in those locations, the bite tab itself is not blocking heat from flowing into the oral cavity.

Figure 7:
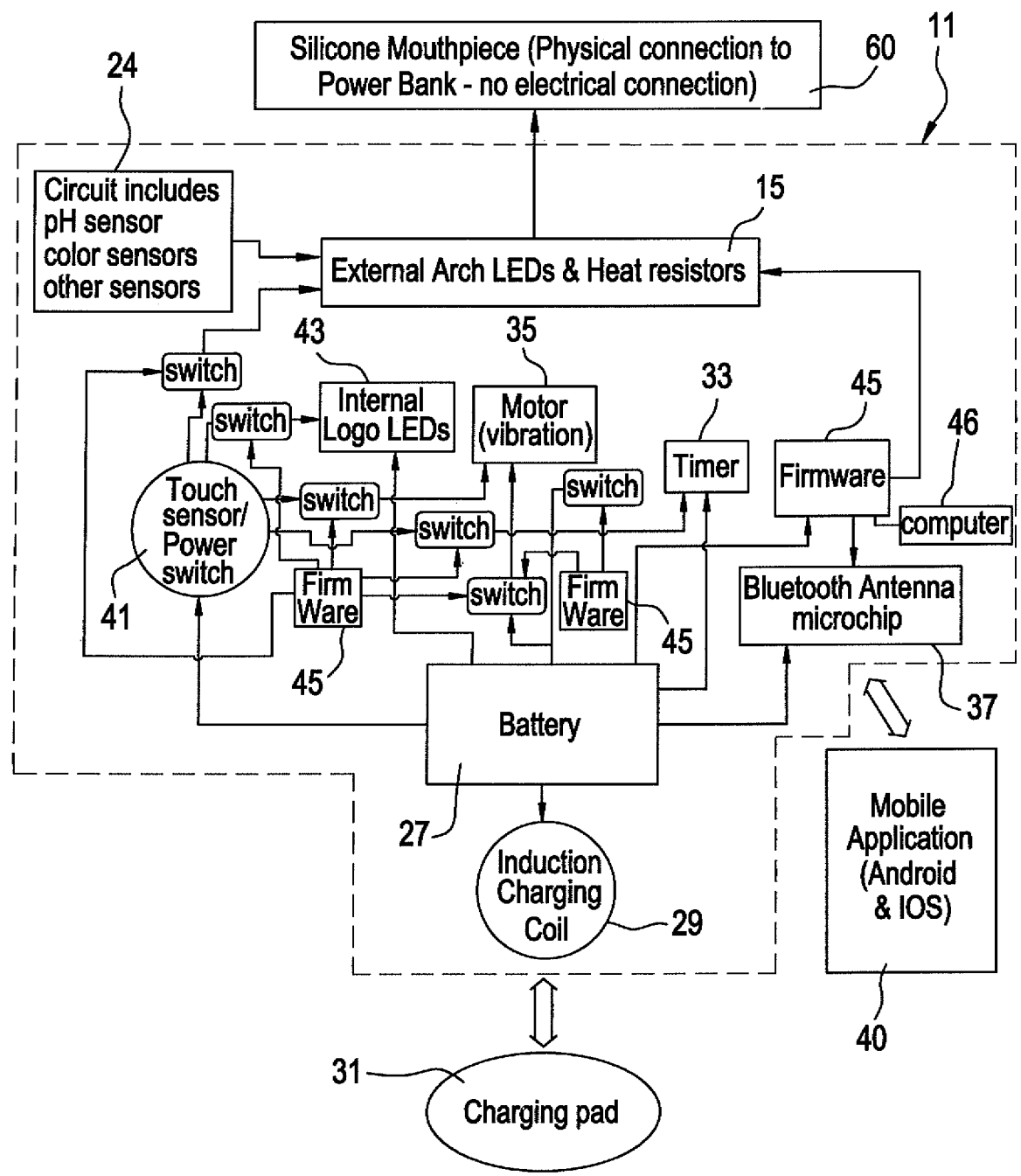
FIG. 7 shows a schematic representation of the circuitry of the control module of the present invention.

Reference is now made to FIG. 7 for an explanation of the electrical circuitry of the present invention. With reference to FIG. 7, within the control module 11, a battery 27 is provided which is electrically connected to an induction charging coil 29 that facilitates charging of the control module battery 27 using a charging pad 31. The battery 27 powers all the systems of the control module 11.

As also seen in FIG. 7, the circuit board 15 is schematically depicted as is the mouthpiece 60. The circuit board 15 is powered by the battery 27 and a timer 33 may be set as understood by those of ordinary skill in the art to time a time period within which the electrical circuit 15 is activated to activate the LEDs 23 and heat resistors 25. If desired, some or all of the LEDs 23 may be activated and deactivated separately and some or all of the heat resistors may be activated and deactivated separately. A motor 35 is provided that includes a mechanism including an offset crank (not shown) that imparts vibration to the control module 11 and provides haptic (tactile) feedback to the mouthpiece 60 when the motor 35 is activated.

The control module 11 also includes a Bluetooth antenna microchip 37 that allows transmission from the control module 11 and receiving of signals from an outside transmitter such as located within a mobile application 40.

A touch sensor 41 is provided in the control module 11 allowing the user to directly control functions of the control module 11 without need for wireless controlling via the mobile application 40. Consecutive touches of the touch sensor 41 cause activation of various features of the system 10 as understood by those of ordinary skill in the art. Also provided are internal logo LEDs 43 which provide indication of modes of operation being undertaken by the system 10 so that the user can confirm that a desired mode of operation has been selected. The circuit board 15 may also include sensors shown in the block 24, including a pH sensor to measure degree of acidity, and a color sensor to sense teeth color.

The pH sensor, for example, may come into contact with a user's saliva when the mouthpiece 60 is placed in the user's mouth, and the pH sensor measures the electrical potential (voltage) produced by the saliva, compares it to the voltage of a reference solution and uses the electrical potential difference to deduce a pH reading of the sample. In the case of this pH sensor system, hydrogen ions from a saliva sample act as the analyte, the sensor receives electrical potential information, transduces a signal to be sent via Bluetooth antenna microchip 37 to be processed by the mobile application 40 and provide data to the end user that may be used to build a custom treatment recommendation.

The color (optical) sensor(s) embedded in circuit 15 and identified in box 24, for example, may align with a subset of a user's teeth when the mouthpiece 60 is placed in the user's mouth. The optical sensor(s) emit a white light directed at the tooth surface and the optical sensor(s) receive the reflected light. The amount of light received is recorded and converted to a current that can then be converted to voltage. Once a voltage has been determined, a signal is transduced and sent via Bluetooth antenna microchip 37 to be processed by the mobile application 40 where it is analyzed to display a digital output of the user's current tooth color corresponding to the received voltage level and provide treatment recommendation(s).

Sensors coming into contact with saliva can detect proteins, electrolytes, drugs, hormones, antibodies, toxins and acidity. With these sensors, we can detect pH, glucose levels, and inflammatory biomarker presence to obtain early warning signs for cardiovascular disease and 120 systemic inflammatory diseases that correlate to oral health as understood by those skilled in the art. The acid/base balance or pH is a direct indicator of health of the mouth. Low pH impacts demineralization of the teeth below a pH of 5.4 and creates an environment for "bad" bacteria to colonize. The mouth is in homeostatic balance of good vs. bad bacteria and the pH of the mouth reflects our nutrition, stress levels, sleep, and home care and genetics.

Today, to obtain such information, users must collect samples of the saliva and send it to a company to get a profile. However, in accordance with the teachings of the present invention, a sensor contained in the universally sized mouthpiece and exposed to saliva allows for constant monitoring. Diseases detected can include but are not limited to diabetes, HIV/AIDS, cancer, Sjogren's syndrome, and can help to understand the personal impacts of prescription drugs on the saliva.

Saliva is the new "blood" of health diagnostics and through the dental office which is the first line of defense for healthcare in the future, we can monitor our patients for both oral health and their overall health.

Firmware schematically designated by the reference numeral 45 can be associated with an internal computer or web/desktop application 46 programmed with desired software to allow storage of information concerning operation of the system 10 as well as transmitting of that information via the Bluetooth and antenna microchip 37 to a remote location such as the mobile application 40 or web/desktop application 46. The mobile application 40 can be either hardwire connected to a computer or wirelessly connected to a computer so that data can be transmitted and saved for future analysis.

In operation, the user touches the Touch Sensor 41 and the Battery 27 powers the Internal Logo LEDs 43 and Motor 35 to provide haptic feedback to the user to notify them that they have powered the device on. The user can connect to the mobile application 40 which can comprise a smartphone via Bluetooth 37 signal sent/received by microchip antenna at this time. The user can then touch the Touch Sensor 41 once more, or select a button in the associated mobile application 40 which can be a smartphone, to power on the External Arch LEDs 23, Heating Elements 25 and Sensor(s) 24. The user can then place Silicone Mouthpiece 60 attached to control module 11 in their mouth. The Silicone Mouthpiece 60 is mechanically placed on the control module 11 with no electrical transfer. The internal Timer 33 automatically powers off the External Arch LEDs 23, Heating Elements 25 and Sensor(s) 24 after, for example, 8 minutes. The Heat resistors 25 reach a maximum temperature of 50° C. (122° F.) before Firmware 45 regulates the temperature downward. The LEDs 23, controlled by Firmware 45, can reach peak wavelengths of either 470 nm (Blue) or 630-700 nm (Red). The LEDs emitting Blue light are used for enhancing the cosmetic whitening treatment. The LEDs emitting Red light of the listed peak wavelengths (630-700 nm) are used for tissue healing and bone modulation for the purpose of orthodontic treatment acceleration. The Battery 27 is connected to a Coil 29 which is recharged by induction when placed on an external Charging Pad 31. The Sensor(s) 24 embedded on the flexible circuit board 15 collect user data, including but not limited to acidity level (pH) and/or teeth color (optical or otherwise), and the data is stored on device memory in computer 46. The Sensor(s) 24 data output is then transmitted via the Bluetooth Antenna microchip 37 and received by the mobile application 40 where it is analyzed to create a custom treatment regimen for the end user.

With reference to FIG. 8, the mobile application 40 is shown as well as a schematically represented computer 46, a data storage cloud 51, a wife interconnection 53, and wireless transmission 55 from the mobile application 40 to the system 10. As understood from FIG. 8, the mobile application 40 can wirelessly control the system 10 via the Bluetooth wireless connection (55) to cause the control module 11 to start and stop, to pause, to set, reset, and control the timer 33, and to facilitate providing a whitening schedule and keeping track of whether the user is adhering to the schedule. Additional information can also be programmed into the mobile application 40 including the ability to provide a listing of dentists who are familiar with the system 10 and for the ability to purchase products such as a replacement mouthpiece 60, a replacement control module 11, or any other components.

In the preferred embodiment of the present invention, the LEDs 23 emit blue light at a wavelength of approximately 470 nm, but as explained above, LEDs emitting red light at a wavelength of 630-700 nm may also be provided. The heat resistors 25 preferably are able to elevate the temperature of the mouthpiece 60 to within the range of 50'C (122° F.). If desired, a wifi or cellular connection can be established between the mobile application 40 and a computer system 46 either directly or via a cloud 51 to facilitate transmission of data to and from the cloud or computer 46 for various purposes including monitoring the function of the system 10, keeping track of whether the user is adhering to a desired or preprogrammed schedule, and any other desirable reason.

The mouthpiece 60 is universally sized to be adaptable to mouths and oral cavities of differing configurations and is made of a flexible plastic material that may be translucent or transparent. The motor 35 (FIG. 7) may be used for haptic user feedback. As explained supra, the control module 11 may be powered on by physical contact with a touch sensor 41 mounted thereon and thereafter may be controlled by sequential physical contact with the touch sensor 41 or by a software application paired with the unit via wireless transmission such as Bluetooth, wifi, etc. The mobile application 40 may be employed to pause activation of the circuit board 15, activate it and deactivate it, and perform other desirable functions as understood by those of ordinary skill in the art.

Through use of the present invention, the user is no longer required to be tethered to a source of electrical power via an electrical conductor incorporated into the device. Rather, the control module 11 may easily be recharged inductively, if desired, and once the battery thereof is charged may operate free of any wired connections to power sources.

As such, an invention has been disclosed in terms of a preferred embodiment thereof with various aspects which fulfills each and every one of the objects of the invention as set forth hereinabove, and provides a new and useful wireless teeth whitening system of great novelty and utility.

Of course, various changes, modifications, and alterations in the teachings of the present invention may be contemplated by those of ordinary skill in the art without departing from the intended spirit and scope thereof.

As such, it is intended that the present invention only be limited by the terms of the appended claims.

The invention claimed is:

1. A combination mouthpiece and control module, comprising:

a) said mouthpiece comprising a transparent or translucent body including a forward facing surface and a rearward facing surface, said body being arcuate in conformance with an oral cavity of a user including a central area and rearwardly extending sides;
b) a bite tab depending rearwardly from said rearward facing surface; and
c) said forward facing surface extending from said central area of said body and including rearwardly extending side surface portions in said rearwardly extending sides, said side surface portions extending rearward from said central area, said forward facing surface forming a part of a recessed area;
d) said recessed area having a forward facing arcuate shape;
e) a control module having a body including a central portion where a circuit board is located, said control module being attached to said mouthpiece with said circuit board adjacent to said forward facing surface of said mouthpiece at said central area of said body, and a source of power connected to said circuit board to controllably supply power to said circuit board;
f) said circuit board including an array of sources of electromagnetic radiation, said sources of electromagnetic radiation being directly exposed to said recessed area;
g) said circuit board including an antenna microchip facilitating transmission from said control module of signals to a remote location and receipt of signals from a remote location;
h) said mouthpiece being separable from said control module such that said mouthpiece can be sterilized; and
i) a device located at said remote location, said device wirelessly communicating with said control module to remotely control operations of said control module.

2. The combination mouthpiece and control module of claim 1, wherein said sources of electromagnetic radiation comprise LEDs.

3. The combination mouthpiece and control module of claim 2, wherein said LEDs shine blue light when activated.

4. The combination mouthpiece and control module of claim 3, wherein said blue light has a wavelength of approximately 470 nanometers.

5. The combination mouthpiece and control module of claim 2, wherein said LEDs shine red light when activated.

6. The combination mouthpiece and control module of claim 5, wherein said red light has a wavelength in the range of 630-700 nanometers.

7. The combination mouthpiece and control module of claim 1, wherein said sources of electromagnetic radiation comprise heating elements.

8. The combination mouthpiece and control module of claim 7, wherein said heating elements comprise heat resistors that may reach a maximum temperature of 122° F. (50° C.).

9. The combination mouthpiece and control module of claim 1, further including a motor contained within said control module which, when activated, imparts vibration to said control module and said mouthpiece.

10. The combination mouthpiece and control module of claim 1, wherein said device comprises a mobile device in which an APP is downloaded to facilitate wireless communication with said control module, said APP programming said mobile device to facilitate wireless control of operations of said control module.

11. The combination mouthpiece and control module of claim 1, wherein said source of power comprises a battery within said control module.

12. The combination mouthpiece and control module of claim 11, further wherein an induction coil is located within said control module and coupled to said battery, whereby said battery may be wirelessly charged.

13. The combination mouthpiece and control module of claim 2, further including a further array of sources of electromagnetic radiation.

14. The combination mouthpiece and control module of claim 13, wherein said sources of electromagnetic radiation in said further array comprise heating elements.

15. The combination mouthpiece and control module of claim 14, wherein said heating elements comprise heat resistors that may reach a maximum temperature of 122° F. (50° C.).

16. A combination mouthpiece and control module, comprising:
a) said mouthpiece comprising a transparent or translucent body including a forward facing surface and a rearward facing surface, said body being arcuate in conformance with an oral cavity of a user including a central area and rearwardly extending sides;
b) a bite tab depending rearwardly from said rearward facing surface; and
c) said forward facing surface extending from said central area of said body and including rearwardly extending side surface portions in said rearwardly extending sides, said side surface portions extending rearward from said central area, said forward facing surface forming a part of a recessed area;
d) said recessed area having a forward facing arcuate shape;
e) a control module having a body including a central portion where a circuit board is located, said control module being attached to said mouthpiece with said circuit board adjacent to said forward facing surface of said mouthpiece at said central area of said body, and a source of power comprising a battery within said control module connected to said circuit board to controllably supply power to said circuit board;
f) said circuit board including a plurality of arrays of sources of electromagnetic radiation, said sources of electromagnetic radiation being directly exposed to said recessed area; and
g) said circuit board including an antenna microchip facilitating transmission from said control module of signals to a remote location and receipt of signals from a remote location;
h) said mouthpiece being separable from said control module such that said mouthpiece can be sterilized; and
i) a device located at said remote location, said device wirelessly communicating with said control module to remotely control operations of said control module.

17. The combination mouthpiece and control module of claim 16, wherein one of said arrays comprises a plurality of LEDs.

18. The combination mouthpiece and control module of claim 16, wherein one of said arrays comprises a plurality of heating elements.

19. The combination mouthpiece and control module of claim 18, wherein another one of said arrays comprises a plurality of LEDs.

20. The combination mouthpiece and control module of claim 19, wherein a third of said arrays comprises a further plurality of heating elements.

21. The combination mouthpiece and control module of claim 14, wherein said LEDs and heating elements engage a surface of said recessed area.

22. The combination mouthpiece and control module of claim 19, wherein said LEDs and heating elements engage a surface of said recessed area.

* * * * *